United States Patent [19]

Bentzen

[11] 4,309,188
[45] Jan. 5, 1982

[54] METHOD FOR THE CLINICAL SEPARATION OF α- AND β-LIPOPROTEINS

[75] Inventor: Craig L. Bentzen, Onex, Switzerland

[73] Assignee: Symphar S.A., Geneva, Switzerland

[21] Appl. No.: 130,625

[22] Filed: Mar. 17, 1980

[30] Foreign Application Priority Data

Oct. 22, 1979 [GB] United Kingdom ............... 36573/79

[51] Int. Cl.³ ............................................ G01N 33/92
[52] U.S. Cl. .................................... 23/230 B; 23/909; 260/112 B
[58] Field of Search ............................ 23/230 B, 909; 260/112 B

[56] References Cited

U.S. PATENT DOCUMENTS 4,039,285  8/1977  Teipel .................................. 23/230 B
4,096,136  6/1978  Ayers et al. ...................... 260/112 B
4,103,685  8/1978  Lupien et al. ...................... 422/44 X
4,178,439  12/1979  Ayers et al. ........................ 536/1 X

OTHER PUBLICATIONS

Castelli et al., Circulation 55, pp. 767–772, 1977.
A. Casu, Ital. J. of Biochem. 28(1) 26, 1979.
Abstracts of the 52nd Scientific Sessions by Alanopovic et al., Abstr. American Society for Study of Atherosclerosis 33rd, 2nd, 1979.
Havel et al., J. of Cl. Invest. 34, 1345, 1955.
Eisenberg, Atherosclerosis Review vol. 1, p. 23, 1976.
Mahley et al., J. of Lipid Research 18, 314, 1977.
Lee, Science 169, 493, 1970.
Durrington et al., Clinica Chemica Acta, 71 (1976) 95–108.
Bachorik et al., Clin. Chem. 22/11, 1828–1834, 1976.
Srinivasan et al., Archives of Biochemistry and Biophysics 170, 334–340, 1975.
Warnick et al., Journal of Lipid Research 19, 65–76, 1978.
Warnick et al., Clinica Chemistry, 25, No. 4, 596, 1979.
Rhoads et al., The New England J. of Med. 294, No. 6, 293, 1976.
Gofman et al., Circulation, 34, 679, 1966.
Henry, Clinical Chemistry 2nd Ed. 1140, 1974.
Curry et al., Clinical Chemistry 24, No. 2, 280, 1978.

Primary Examiner—Arnold Turk
Attorney, Agent, or Firm—Young & Thompson

[57] ABSTRACT

This invention relates to a separation method comprising the introduction of a sample of serum or plasma into a microcolumn containing a support which has a sulfated polysaccharide, preferably heparin, covalently bound to it so as to remove from said sample the β-lipoproteins by binding thereof to this ligand, followed by washing the microcolumn with a first pH buffered solution and collecting the eluant representing a first fraction containing the α-lipoprotein portion of the sample. Then the microcolumn is washed wth a second pH buffered solution so as to release the ligand-bound β-lipoproteins and to recover a second fraction containing the β-lipoprotein portion of the sample. Afterwards, it is possible to separately determine the α- and β-lipoprotein-cholesterol, as well as the respective α/β ratios of phospholipids, triglycerides and various apoproteines, and to calculate the respective ratios α/β, all useful as clinical diagnostic indexes and allowing to obtain a complete lipoprotein profiling.

The invention also concerns a kit comprising in a transportable box all the implements and reagents duly prepared so as to easily and quickly carry out the above method.

13 Claims, No Drawings

METHOD FOR THE CLINICAL SEPARATION OF α- AND β-LIPOPROTEINS

The present invention relates to a new method for the clinical separation of α-lipoproteins (primary component of high density lipoproteins or HDL) and β-lipoproteins (primary component of very low density lipoproteins or VLDL and low density lipoproteins or LDL) in serum or plasma using a microcolumn technique. This invention also relates to a kit comprising the materials and products for carrying out the above mentioned separation method and respective analysis.

This method of separating α and β lipoproteins in two separate soluble fractions allows one to proceed directly with a complete profiling of the two major lipoprotein classes by quantitating cholesterol, phospholipids, triglycerides and apoprotein concentrations in the respective fractions. In the case of cholesterol, the resulting ratio of α-lipoprotein cholesterol (herein after called α LP-c) to β-lipoprotein cholesterol (herein after called β LP-c)(αLP-c)/(βLP-c) furthermore can be used by the clinicians as an important diagnostic index (Castelli et al. Circulation 55, 767, 1977).

In addition, there is published data to support the growing concept that the respective α/β ratios of phospholipids, various apoproteins and triglycerides reflect membrane fluidity and lipid turnover (see A. Casu, Italian Journal Biochemistry 28, 26, 1979; Alaupovic et al., Abst. American Society for the study of Atherosclerosis 33rd, 2, 1979). Therefore, the total lipoprotein profile can be used in evaluating the existance of or potential of individuals for developping atherosclerosis and coronary heart disease as well as a method for monitoring therapeutic improvement.

The conventional method for separating lipoproteins is the ultracentrifugation method described by R. J. Havel et al, J. Clin. Invest. 34, 1345, 1955 and further developped by BECKMAN as the "Lipoprotein Profiling System." The disadvantages of this type of method are that it is time consuming, expensive (costly equipment for ultracentrifugation) and lacking of specificity since the separation is carried out purely according to density (see S. Eisenberg, Atherosclerosis Reviews, Vol. 1, p. 23, 1976, Ed. R. Paoletti and A. M. Goho Jr., Raven Press, New York). In addition, ultracentrifugation can alter the physical as well as the chemical properties of the lipoproteins (see R. W. Mahley and K. S. Holcombe, J. of Lipid Res. 18, 314, 1977).

A second type of known separation methods consists in the immunological methods, such as radial immunodiffusion (see R. S. Lee, Sciences 169, 493, 1970), rocket immunoelectrophoresis (see P. N. Durrington et al., Clin. Chem. Acta 71, 95, 1976) and radio immuno assay (RIA). However, all these immunological methods are also expensive (specialized equipment), time consuming and in some cases the antibody lacks the specifity so that the method cannot be used for producing a relevant clinical index. Furthermore, since the procedure for preparing the antibodies is difficult and costly the price of anti-human lipoprotein is likewise expensive.

A method is also known for determining HDL cholesterol which involves the precipitation of apo-β-containing lipoproteins by divalent cations with polysaccharides, for example with $MnCl_2$ and sodium heparin (see A. S. Bachorik et al., Clin. Chem. 22, 1828, 1976 and S. R. Srinivasan et al., Arch. Biochem. Biophys. 170, 334, 1975). This method is inexpensive and rapid, but the primary objection thereto is the lack of specificity of precipitation. For example, Srinvasan et al. have observed that precipitation of α-lipoproteins (HDL) may occur when the $Mn^{++}$ concentration is increased. In addition, recent works carried out by G. R. Warnick and J. J. Albers, J. of Lipid Res. 19, 65, 1978 and Clin. Chem. 25/4, 596, 1979, demonstrate that there is an incomplete sedimentation of β-lipoproteins from plasma samples of hypertriglyceridemic patients when using the normal values of $Mn^{++}$ heparin.

Furthermore, recent studies have confirmed that HDL cholesterol is an independent risk lowering factor. That is to mean, there is a decreased prevalence and incidence of coronary heart disease among persons having high HDL-cholesterol levels (see G. R. Warnich et al., Clin. Chem. 2514, 596, 1979, G. F. Rhoads et al., N. Engl. J. Med. 294, 293, 1976 and W. P. Castelli et al., Circulation 55, 767, 1977). With increased awareness of the importance of the α-lipoprotein cholesterol as an independent negative risk factor in cardiovascular disease, there is a strong demand for a selective quick and inexpensive method for separating and quantitatively measuring α-lipoproteins, and which of course further allows individual quantitation of the β-type lipoprotein cholesterol as the second major step. As a matter of fact, augmented levels of β-lipoprotein cholesterol are observed with the development of cardiovascular disease and are often associated with bad dietary habits (see J. W. Gofman et al., Circulation 34, 679, 1966).

Therefore, the present inventor have developed a new, simple, rapid and inexpensive microcolumn method for the clinical separation of α and β-lipoproteins in serum or plasma, which is based on the specificity of sulfated polysaccharides and especially heparin for binding the β-type lipoproteins.

Consequently, a first object of this invention consists in such a method comprising the introduction of a sample of serum or plasma into a microcolumn containing a support which has a sulfated polysaccharide, preferably heparin, bound to it so as to remove from said sample the β-lipoproteins, by binding thereof to this ligand, followed by washing the microcolumn with a first pH buffered solution and collecting the eluent representing a first fraction containing the α-lipoprotein portion of the sample, and further washing the microcolumn with a second pH buffered solution, so as to release the ligand-bound-β-lipoproteins and recover a second fraction containing the β-lipoproteins portion of the sample.

A second object of this invention is constituted by the application of the above method to the determination of the ratio of α-lipoprotein-cholesterol to β-lipoprotein-cholesterol which is usable as a clinical diagnostic index.

A third object of this invention is the application of the above method to the quantitative determination of α and β lipoprotein lipids and protein components such as phospholipids, triglycerides, apo C-III- and apo E-proteins which allow a complete lipoprotein profile which is clinically and diagnostically useful.

A fourth object of this invention is a kit for carrying out the above separation method which comprises in a transportable box a rack holder, a number of microcolumns containing a sulfated polysaccharide preferably heparin, bound to an insoluble support, eventually held in position by a special inert sponge filter, and containers containing appropriate preweighed chemicals for preparing the respective pH buffered solutions.

The support being covalently bound with ligand is preferably of agarose such as Sepharose.

Typically the heparin being bound to the agarose support is preferably in the proportion of 6–10 mg dry weight heparin (porcine origin) approximately 150 USP JA units/mg to 1 gram of wet weight agarose.

The solutions A and B represent different molarity proportions of sodium chloride, for example respectively for A a range of 0.140 to 0.165 and for B a range of 0.5 to 1.5, and contain buffer salts such as sodium phosphate salts producing a pH range of 6.0–6.5.

The present invention will be further illustrated and described in a more detailed manner by reference to the following example.

EXAMPLE

Each microcolumn containing 0.6% heparin covalently bound to a Sepharose support is placed vertically in the rack holder and prepared by washing with 3–5 ml of the buffer solution A (pH=6.2; with 0.15 M sodium chloride) and allowed to drip until no solution remains on top of the column support.

Next, 500 $\mu$l of the serum or plasma sample to be analysed are added to the column and allowed to completely enter the column support.

Then, 2 ml of the buffer solution A are added to the column and the entire eluant collected. This collected eluant of 2.5 ml contains the $\alpha$-lipoproteins of the sample (Tube 1; $\alpha$-fraction).

Three ml of the buffer solution B (pH=6.5; with 0.5 M sodium chloride) are then passed through the column into another collection tube (Tube 2); this solution contains the $\beta$-type lipoproteins ($\beta$-fraction).

For example to obtain the $\alpha$LP-c/$\beta$LP-c ratio the appropriate aliquots of Tube 1 and Tube 2 are taken, depending upon the cholesterol test being used, and analyzed for cholesterol content. Most types of cholesterol analysis can be used, for example the cholesterol determination by the enzymatic cholesterol oxidase reaction according to R. J. Henry and M. Henry, Clin. Chem. 2nd Ed., 1440, 1974, Harper and Row Publ., New York, which can be obtained for example from Merck Diagnostica product no. 14350 or Boehringer Diagnostics—product no. 172626, etc.

A specific example will be described to further illustrate the specificity of the method according to the invention for producing pertinent lipoprotein profile indexes which can be clinically useful.

EXAMPLE

Fresh human serum was obtained from a normal individual. The respective $\alpha$ and $\beta$ fractions were obtained daily for 7 consecutive days exactly as previously described.

Cholesterol (c)

For obtaining the ($\alpha$LP-c)/($\beta$LP-c) ratio one hundred microliters of both the $\alpha$ and $\beta$ fractions were taken and mixed with 2 mls of the cholesterol reagent, according to "Cholesterol Monotest" (Chod-PaP-Methode) No 237 574 of Boehringer Mannheim.

After 30 minutes incubation at room temperature the reaction mixture was read in a 1 cm cuvette at Hg 546 nm.

Total cholesterol: 0.02 ml+2 ml reagent=>O.D.$\times$924=c.mg/dl $\alpha$:0.100 ml+2 ml reagent=>O.D.$\times$924=c.mg/dl $\beta$:0.100 ml+2 ml reagent=>(O.D.$\times$924$\times$3)/2.5=c.mg/dl blank: 0.1 ml sol. A+2 ml reagent The individual results in mg/100 ml, statistics and corresponding $\alpha/\beta$ ratios for the 7 day study are listed in Table I-A.

Phospholipids (PL)

The phospholipid values (PL) were determined in both $\alpha$ and $\beta$ fractions using the Boehringer "Combination Test Phosphor/Phospholipid" (ref. no 124 974). One ml of each fraction is taken and mixed with 4 ml of trichloroacetic acid (20%) to precipitate all lipoproteins. The tubes were centrifuged at 3000 rpm for 15 minutes and the supernatant pipetted off. Amounts of 0.5 ml perchloric acid and 0.2 ml $H_2O_2$ were added to the tube and heated for 20 minutes at 180°–200° C. in a heating block. After the tubes were cooled, 2 ml of distilled water 1 ml, of 0.28 N ammonium vanadate (solution no. 1) and 1 ml of 2.5 N ammonium molybdate (solution no. 2), were added and mixed. After 10 minutes incubation at room temperature the reaction mixture was read in a 1 cm cuvette at Hg 405 nm.

Tot PL: 0.01 ml sample => $\frac{\text{O.D. sample}}{\text{O.D. std}} \times 12.5$ = c.mg/dl $\alpha$ PL: 1.0 ml sample => $\frac{\text{O.D. sample}}{\text{O.D. std}} \times 12.5$ = c.mg/dl $\beta$ PL: 1.0 ml sample => $\frac{\text{O.D. sample}}{\text{O.D. std}} \times 15.0$ = c.mg/dl The individual results in mg/100 ml, statistics, and corresponding $\alpha/\beta$ ratios for the 7 day study are listed in Table I-B.

Triglycerides (TG)

The triglyceride values (TG) were determined in both $\alpha$ and $\beta$ fractions using the Boehringer "Combination Test Triglyceride" (ref. no 126012). An amount of 20 ml of each $\alpha$ and $\beta$ fraction was mixed with 1 ml of prepared reagent (1+2+3) and incubated at room temperature for 10 minutes after which a first O.D. (E1) at Hg 340 nm was measured. Then 5 $\mu$l of reagent 4 was added and incubated at room temperature for an additional 10 minutes after which a second O.D. (E$_1$) was measured. The D.O's (ER$_1$) and (ER$_2$) values were simultanously obtained for a reference blank.

Total TG: 0.020 ml sample=>$\Delta$E--$\Delta$ER$\times$711=mg/dl $\alpha$TG: 0.200 ml sample=>$\Delta$E--$\Delta$ER$\times$355.5=gl/dl $\beta$TG: 0.200 ml sample=>$\Delta$E--$\Delta$ER$\times$426.6=mg/dl The individual results in mg/100 ml, statistics, and corresponding $\alpha/\beta$ ratios for the 5 day study are listed in Table I-C.

Apoproteins

Quantification of various apoproteins, i.e. A-I, A-II, B, C-I, C-II, C-III and E, can be carried out by electroimmunoassay, radioimmunoassay, and radial immunodiffusion assay when appropriate antiserum is available according to the general technics used by the Alaupovic group (Curry, et al. Clin. Chem. 24 (2), 280, 1978).

TABLE I

A. CHOLESTEROL

| Test (day) | Tot. C. | $\alpha$C (Mg/100ml) | $\beta$C | $\alpha/\beta$ index | % recovery |
|---|---|---|---|---|---|
| 1 | 230.5 | 66 | 161 | 0.415 | 98.4 |
| 2 | 231 | 73 | 175 | 0.42 | 107.2 |
| 3 | 241 | 73 | 170 | 0.43 | 99.5 |
| 4 | 241 | 70 | 170 | 0.41 | 98.6 |
| 5 | 229 | 69.5 | 164 | 0.42 | 101.6 |

TABLE I-continued

| | | | | | |
|---|---|---|---|---|---|
| 6 | 240 | 74 | 166 | 0.44 | 99.7 |
| 7 | 245 | 71 | 173.5 | 0.41 | 98.9 |
| mean value | 236.8 | 70.9 | 168.5 | 0.42 | 100.5 |
| | ±6.4 | ±2.7 | ±5 | ±1.1 | ±3.1 |

B. PHOSPHOLIPIDS

| Test (day) | Tot. PL | αPL (mg/100 ml) | βPL | α/β index | % recovevy |
|---|---|---|---|---|---|
| 1 | 217 | 118 | 98 | 1.2 | 100 |
| 2 | 212 | 111 | 94.5 | 1.17 | 97 |
| 3 | 215 | 105.5 | 96 | 1.09 | 94 |
| 4 | 220 | 119 | 95.5 | 1.24 | 97.5 |
| 5 | 265 | 143.5 | 115.5 | 1.24 | 98 |
| 6 | 270 | 136 | 116 | 1.17 | 93.5 |
| 7 | 260 | 141 | 118.5 | 1.19 | 100 |
| mean value | 237 | 124.8 | 104.8 | 1.18 | 97.1 |
| | ±26.4 | ±15.2 | ±11.1 | ±0.05 | ±2.4 |

TRIGLYCERIDES

| Test (day) | Tot. TG | αTG (mg/100 ml) | βTG | α/β index | % recovery |
|---|---|---|---|---|---|
| 1 | 67.5 | 27 | 34 | 0.79 | 90 |
| 2 | 74.6 | 25 | 39.6 | 0.63 | 87 |
| 3 | 72.5 | 25.5 | 39 | 0.65 | 90 |
| 4 | 87 | 27 | 40.5 | 0.66 | 78 |
| 5 | 86 | 25 | 40.5 | 0.61 | 76 |
| mean value | 77.5 | 25.9 | 38.7 | 0.668 | 84 |
| | ±8.6 | ±1.09 | ±2.4 | ±0.07 | ±6.7 |

The distribution and composition of lipoproteins in various disease states in humans was studied as early as 1955 by Havel, R. J. et al. (J. Clin. Invest. 34, 1345, 1955.). When examining their results (Table II), it becomes clear that changes in composition and distribution (ratio) of lipids especially cholesterol and phospholipids among the major lipoprotein classes is indicative of existing disease states. (See Table II on following page).

Of course, the kit according to the invention can also contain the necessary reagents for such determination as described above.

TABLE II*

| Diagnosis | LP Cholesterol Index α LP-c/β LP-c × 100 | LP Phospholipid Index α LP-PL/β LP-PL |
|---|---|---|
| Normal | 38.5 | 1.21 |
| Post myocardial infarction | 25.9 | 0.77 |
| Idiopathic hyperlipidemic | 7.8 | 0.43 |
| Xanthoma tendinasum | 18.1 | 0.55 |
| Nephrotic syndrom | 8.2 | 0.13 |
| Infectious hepatitis | 5.6 | 0.21 |
| Obstructive jaundice | 7.1 | 0.27 |
| Primary biliary cirrhosis | 4.0 | 0.11 |

*results obtained from Havel et al. JCI 34, 1345, 1955

This invention presents the following advantages especially with regards to the known methods recited in the introductory part.

The separation method is inexpensive, since the microcolumns can be regenerated at least 20–30 times, and there would be no additional expenses for equipment. For example, no equipment is needed for separating the lipoproteins such as centrifuges or electrophoretic apparatus.

The separation method is quick, since at least 30 samples can be run at the same time and requires 45 minutes to obtain the α and β fractions followed by 0.5-2 hours depending upon the test to be performed (cholesterol 30 min.)

Both α and β lipoproteins remain soluble which allows a direct analysis of the respective isolated lipid and protein components (this is not the case for precipitation methods).

The volume of plasma sample needed is small (about 500 μl).

This method is more reliable for obtaining an accurate and reproducible α and β ratio (not merely by mathematical subtraction or comparison with total serum values).

The αLP/βLP index is useful to clinicians for evaluating the particular cardiovascular conditions of the patients. Simple screening of many individuals and patients would allow an earlier diagnostic and probably initiate the dietary or therapeutic treatment needed.

The equipment for carrying out the separation method is very simple, inexpensive and can be presented as a kit in a transportable box.

While the invention has been described in detail and with reference to specific embodiments thereof, it will be apparent to one skilled in the art that various changes and modifications can be made therein without departing from the spirit and scope thereof.

I claim:

1. A method for the clinical separation of α-lipoproteins from β-lipoproteins and for the determination of the ratio of α-lipoproteins to β-lipoproteins in serum or plasma free from added divalent cations, comprising introducing a sample of serum or plasma free from added divalent cations into a microcolumn containing heparin bound to agarose so as to remove from said sample the β-lipoproteins by binding thereof to this ligand, washing the microcolumn with a first pH-buffered solution free from added divalent cations and collecting the eluant as a first fraction containing the α-lipoprotein portion of the sample, subsequently washing the microcolumn with a second pH-buffered solution free from added divalent cations that releases the ligand-bound β-lipoproteins and collecting the eluant as a second fraction containing the β-lipoprotein portion of the sample, analyzing the first fraction for α-lipoprotein, analyzing the second fraction for β-lipoprotein, and using said analyses to calculate the ratio of α-lipoproteins and β-lipoproteins in said sample.

2. A method as claimed in claim 1, in which there is about 0.6 to 1% by weight of heparin covalently bound to said agarose.

3. A method as claimed in claim 1, and analyzing said first and second fractions for α-lipoprotein-cholesterol and β-lipoprotein-cholesterol, respectively.

4. A method as claimed in claim 1, and analyzing said first and second solutions for α-lipoprotein-phospholipid and β-lipoprotein-phospholipid, respectively.

5. A method as claimed in claim 1, and analyzing said first and second solutions for α-lipoprotein-triglycerides and β-lipoprotein-triglycerides, respectively.

6. A method as claimed in claim 1, in which said sample is about 0.5 ml in volume.

7. A method according to claim 1, in which said first and second solutions contain respectively 0.140 to 0.165 M and 0.5 to 1.5 M sodium chloride, as well as buffer salts producing a pH range of 6.0 to 6.5.

8. A method according to claim 7, in which said first solution has a pH of about 6.2 and said second solution has a pH of about 6.5.

9. Kit for carrying out the separation method according to claim 1, comprising in a transportable box, a rack holder, a number of microcolumns containing heparin bound to agarose free from added divalent cations, and containers containing the respectively first and second pH buffered solutions free from added divalent cations.

10. Kit according to claim 9, in which the microcolumns are of a type comprising an inert filter for holding the agarose in position.

11. Kit according to claim 9, in which about 0.6 to 1.0% in weight of heparin is covalently bound to the agarose.

12. Kit according to claim 9, in which said first and second buffered solutions contain respectively 0.140 to 0.165 M and 0.5 to 1.5 M sodium chloride, as well as buffer salts, preferably of sodium phosphate, producing a pH range of 6.0 to 6.5.

13. Kit according to claim 9 further comprising containers containing reagents for performing cholesterol, phospholipids and/or triglycerides determinations.

* * * * *